United States Patent [19]

Tanaka et al.

[11] Patent Number: 4,662,748
[45] Date of Patent: May 5, 1987

[54] APPARATUS FOR MEASURING LUMINESCENCE LIFETIME

[75] Inventors: Masaru Tanaka; Kiyoaki Hara; Issei Yokoyama, all of Kyoto, Japan

[73] Assignee: Horiba, Ltd., Kyoto, Japan

[21] Appl. No.: 746,565

[22] Filed: Jun. 19, 1985

[30] Foreign Application Priority Data

Jun. 26, 1984 [JP] Japan .................. 59-132223

[51] Int. Cl.⁴ .................. G01J 3/443; G01N 21/64
[52] U.S. Cl. .................. 356/317; 250/458.1
[58] Field of Search .................. 356/317, 318; 250/458.1, 459.1, 461.1, 365

[56] References Cited

U.S. PATENT DOCUMENTS

4,563,588  1/1986  Tanaka .................. 250/458.1

FOREIGN PATENT DOCUMENTS

3400296 12/1984 Fed. Rep. of Germany .
57-137843  8/1982 Japan .
59-72049   4/1984 Japan .

OTHER PUBLICATIONS

Kinoshita et al., *Rev. Sci. Instrum.*, 52(4), Apr. 1981, p. 572.
Meltzer et al., *Appl. Optics*, vol. 16, No. 5, May 1977, p. 1432.
West et al., *Am. Lab.*, vol. 8, No. 11, Nov. 1976, p. 77.
Leskovar et al., *Rev. Sci. Instrum.*, vol. 47, No. 9, Sept. 1976, p. 1113.

*Primary Examiner*—F. L. Evans
*Attorney, Agent, or Firm*—Wenderoth, Lind & Ponack

[57] ABSTRACT

Two sets of TACs are simultaneously operated by a start pulse, one set of TACs using a photoelectron pulse due to an excited light from a sample as a stop pulse, and the other set of TACs using a photoelectron pulse due to a fluorescence from the sample as a stop pulse. Each TAC outputs a voltage proportional to the time from the start of action to the receiving of the stop pulse and an excitation light shape and a luminescence transient shape are simultaneously measured on the basis of output voltages from the TACs. A variable offset voltage is added to an output of at least one of the two sets of TACs and the excitation light shape and the luminescence transient shape are displayed on a two-picture synthetic display.

1 Claim, 5 Drawing Figures

APPARATUS FOR MEASURING LUMINESCENCE LIFETIME

BACKGROUND OF THE INVENTION

1. Field of the Invention

The present invention relates to an apparatus for measuring the luminescence lifetime of a sample on the basis of the measurement of the transient waveshape of light radiated from the sample excited by a pulse light, in particular the present invention relates to an apparatus for measuring the luminescence lifetime of a sample having a luminescence lifetime which is not as long as a pulsewidth of an excitation light.

2. Description of the Prior Art

Since, in the case where the luminescence lifetime of a sample is not as long as a pulsewidth of an excitation light, the luminescence shape is dependent upon the excitation light, and it is necessary to measure both a fluorescent shape $I_{(t)}$ and an excitation light shape $P_{(t)}$ and to obtain the true luminescence shape $G_{(t)}$ by the deconvolution operation to determine the luminescence lifetime. Here, the deconvolution operation is an operation in which $G_{(t)}$ is calulated by the following convolution integral equation (1):

$$I_{(t)} = \int_0^t P_{(t')}G(t - t')dt' \qquad (1)$$

When $I_{(t)}$ and $P_{(t)}$ are measured at different times, the excitation light shape $P_{(t)}$ is different from that at the time when $I_{(t)}$ was measured, whereby an error is produced in the luminescence lifetime analysis. Accordingly, it is desirable to measure $P_{(t)}$ and $I_{(t)}$ at the same time.

Such an apparatus for measuring $P_{(t)}$ and $I_{(t)}$ at the same time is disclosed in Japanese Laid-Open Patent Application No. 59-72049/1984 (U.S. patent application Ser. No. 539,680) by the present applicant. This apparatus is provided with a time to amplitude converter (hereinafter referred to as a TAC) for use in the measurement of an excitation light shape and a TAC for use in the measurement of a transient shape, these two TACs being simultaneously operated by means of a start pulse; one TACs uses the photoelectron pulses due to the excitation light as stop pulses, and the other TAC uses the photoelectron pulses due to the emission from the sample as stop pulses; both TACs output voltages proportional to the time from the start of action to the receiving of the stop pulses, whereby the excitation light shape $P_{(t)}$ and the luminescence transient shape $I_{(t)}$ are measured at the same time on the basis of outputs from both TACs. However, since the length of a light passage for measuring $P_{(t)}$ is different from that of a light passage for measuring $I_{(t)}$, even though it is possible to carry out the measurement of $P_{(t)}$ and $I_{(t)}$ at the same time in the above described manner, it was found that the luminescence lifetime could not be accurately measured on account of the following reason:

The stop pulse of the TAC for use in the measurement of the excitation light shape is produced by an optical detector receiving a light from the light source while the stop pulse of the TAC for use in the measurement of the luminescence transient shape is produced by an optical detector receiving the emission from the sample. But, in general, the length of the light passage from the light source to the former optical detector is not equal to the length of the light passage from the sample to the latter optical detector. Now, provided that there is a difference in length of 10 cm between the light passages, this difference in length leads to a time difference of 0.3 nsec. This time difference leads to the shift of the difference between times when two stop pulses are added to a TAC. As a result, the time axis of the excitation light shape is shifted from the time axis of the fluorescence shape by 0.3 nsec, whereby the accurate measurement of the luminescence lifetime becomes impossible.

A method, in which a variable delay element is provided at an input side of one of the TACs and the delay time of this element is adjusted, can be thought of for the general measurement for eliminating such a shift between time axes. However, the variable delay element, which can be used for the place through which a high-speed pulse such as a stop pulse passes, has disadvantages in that it is extremely expensive, and its operating location being limited due to the passage of the high-speed pulse there-through, and is difficult to handle.

SUMMARY OF THE INVENTION

It is an object of the present invention to provide a novel apparatus which is simple in construction and which is capable of completely eliminating the shift between time axes due to the difference between the length of the light passage of the excitation light shape and that of the luminescence transient shape.

In order to achieve the above described object, the present invention provides an apparatus for measuring the luminescence lifetime, in which two TACs are simultaneously operated by means of a start pulse; one TAC uses the photoelectron pulses due to the excitation light as stop pulses, and the other TAC uses the photoelectron pulses due to the emission from the sample as stop pulses, both TACs output voltages proportional to the time from the start of action to the receiving of the stop pulse, whereby the excitation light shape and the luminescence transient shape are measured at the same time on the basis of an output voltage of each TAC; a variable offset voltage having a range adaption is added to an output side of the least one of said two TACs and the excited light shape and the luminescence transient shape are simultaneously displayed on a two-picture synthetic display.

An apparatus for measuring the luminescence lifetime according to the present invention is constructed in the above described manner, so that it has the following effects:

(1) Even though the length of the light passage is changed due to the change of a monochromator, the installation thereof, the removal thereof and the like, the correction can be easily carried out.

(2) Since an offset voltage, which is a direct current voltage, is sufficient for the matching of time axes, an expensive delay element is not required, whereby an inexpensive construction is effected, and a variable width which is much greater than that of the usual delay element is available. In particular, if the offset voltage is adapted to change to even a negative voltage, the adjustment can be carried out at a range in which the usual delay element cannot be adjusted.

(3) Since the offset voltage having the range adaption is added, the readjustment is not required even though the measuring range is changed.

(4) Since a direct current voltage is sufficient for the offset volate, electrical influences do not effect for the delay element, even though an extension line is used, whereby the installation location is not limited. Accordingly, the present invention can be simply added to previously installed apparatus.

BRIEF DESCRIPTION OF THE DRAWINGS

The drawings show one preferred embodiment of the present invention, in which.

DESCRIPTION OF THE PREFERRED EMBODIMENT

Figure 1:
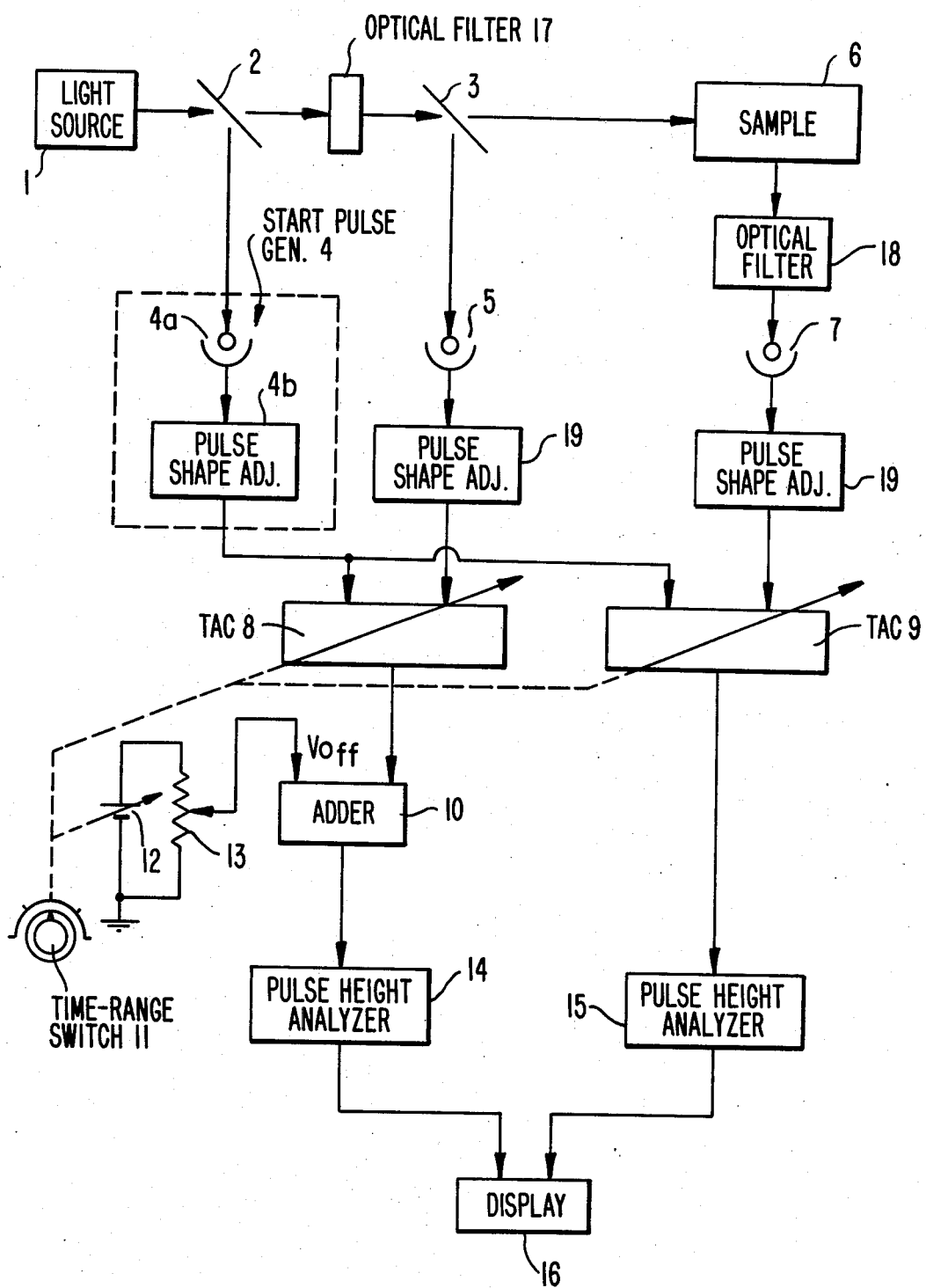
FIG. 1 is a general block diagram.

Referring now to FIG. 7 showing one preferred embodiment of an apparatus for measuring the luminescence lifetime according to the present invention, element (1) designates a light source for radiating a pulsed excitation light; elements (2) and (3) are splitters for dividing the pulsed excitation light into two parts, and element (4) is a means for generating a start pulse as the standard time of the pulse excitation light and consists of a photomultiplier (4a) and a pulse shape-adjusting circuit (4b). Element (5) is an optical detector, for example, a photomultiplier, for receiving the excitation light divided into two parts by the beam-splitter (3) and for radiating a photoelectron pulse; element (6) is a sample on which the rest of the excitation light divided into two parts by the beam-splitter (3) is radiated; element (7) is an optical detector, for example, a photomultiplier, for receiving a fluorescence emitted from said sample (6) and for radiating a photoelectron pulse; element (8) is a TAC for use in the measurement of an excitation light, and element (9) is a TAC for use in the measurement of a fluorescence. Both TACs (8) and (9) are simultaneously operated by a start pulse emitted from said means (4) for generating a start pulse; the TAC (8) uses a photoelectron pulse from the optical detector (5) as a stop pulse, and the TAC (9) uses a photoelectron pulse from the optical detector (7) as a stop pulse; both TACs outputting voltages proportional to the time from the start of action to the receiving of the stop pulse.

In this case, since one TAC can count only one photoelectron pulse, a multi-channel construction is provided for each of the TACs (8) and (9) so that a plurality of photoelectron pulses, which are in turn emitted from the optical detectors during one radiation time, may be counted one by one by means of a TAC for each channel. Such a multi-channel construction is also disclosed in Japanese Laid-Open Patent Application No. 137843/1982 is known to those skilled in the art.

Figure 2:
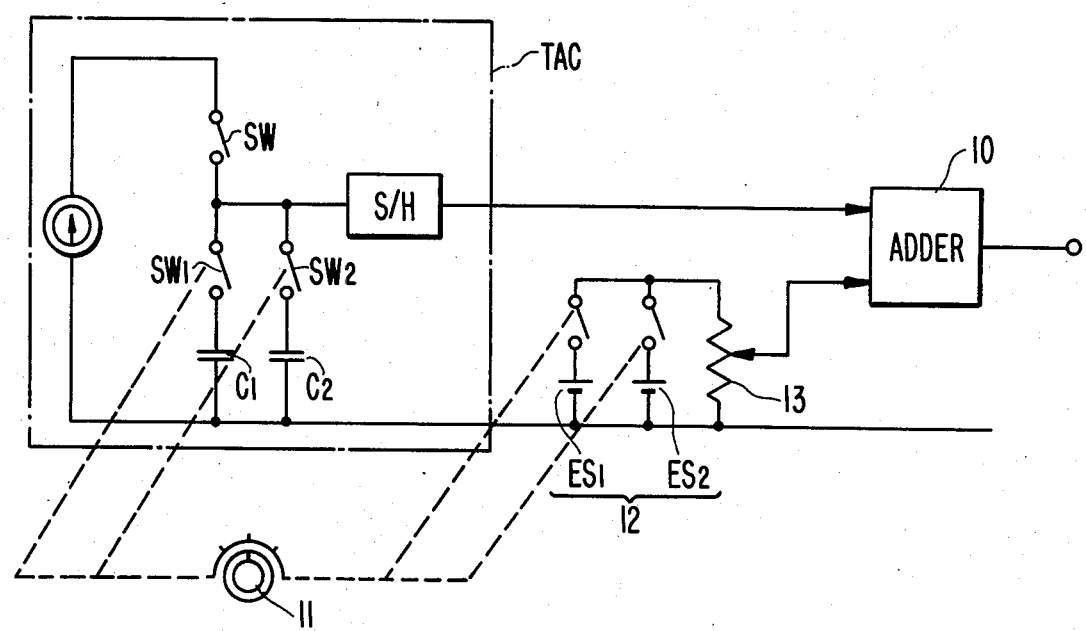
FIG. 2 shows a construction generating an offset voltage having a range adaption.

Element (10) is an adder for example, adder LF 411 ACH manufactured by National Semiconductor Corporation for adding a variable offset voltage $V_{off}$ to an output voltage of the TAC (8). The variable offset voltage $V_{off}$ is generated by means of a DC voltage generator (12) interlocked with a time-range switch (11) and a correcting potentiometer (13). The shift between two waveforms on a time-axis can be eliminated by adding the variable offset voltage $V_{off}$ to an output of one of the TACs since the shift on the time-axis at an input of the TAC appears as a shift on the voltage-axis at an output of the TAC. Said time-range switch (11) changes the offset voltage in a matching manner to the measuring range and has such a construction that DC voltages ES1 and ES2 are changed-over in an interlocking manner with range-changing over switches SW1 and SW2 and changing-over changing capacitors $C_1$ and $C_2$ in the TAC, as shown in FIG. 2.

In this case, for example if the capacitors $C_1$ and $C_2$ have a relationship of $C_2 = 10 \times C_1$ therebetween, then ES1 and ES2 are set so that the relationship of ES2 = (1/10)ES1 is correct. If so, a readjustment is not required even though the range was switched over by correcting the shift on the time-axis for one range whereby the system is very easy to use. In addition, although the offset voltage $V_{off}$ is added to the output of TAC (8) for use in the measurement of the excitation light, it may be added to an output of another TAC or to outputs of both TACs.

Elements (14) and (15) are multichannel pulse height analyzers which are respectively constructed by an A-D converter AD-578 manufactured by Analog Device Corp., a spectrum memory HM 6116-4 manufactured by Hitachi Ltd. and a pre-settable counter 74LS161 manufactured by Texas Instrument Corp; one analyzer (14) receives an output voltage from TAC (8) to produce an excitation light shape and the other analyzer (15) receives an output voltage from TAC (9) to produce a luminescence transient shape. Element (16) is a two-picture synthetic display, for example a CRT LD-20592 manufactured by Nippon Electric Co., Ltd., for simultaneously displaying the excitation light shape produced by said multichannel pulse height analyzer (14) and the luminescence transient shape produced by said multichannel pulse height analyzer (15). Since the two-picture synthetic display simultaneously displays two shapes, it is necessary for the two-picture synthetic display (16) to be capable of distinguishing between both shapes. For example, a color CRT or the like can be used. Elements (17) and (18) are spectrometric means (for example, an optical filter or a monochromator), and element (19) is designating a pulse shape-adjusting circuit for example, a discriminator LM 361N manufactured by National Semiconductor Corp.

Figure 3A:
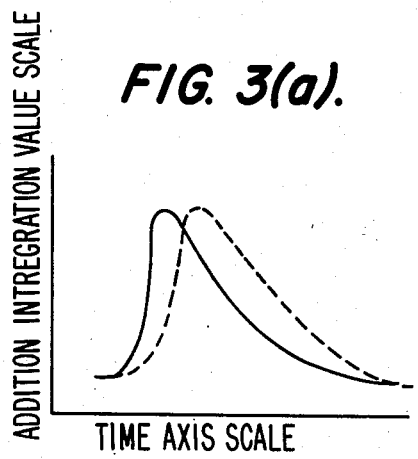
FIG. 3(a), 3(b) and 3(c) show two shapes displayed on a two-picture synthetic display.
Figure 3B:
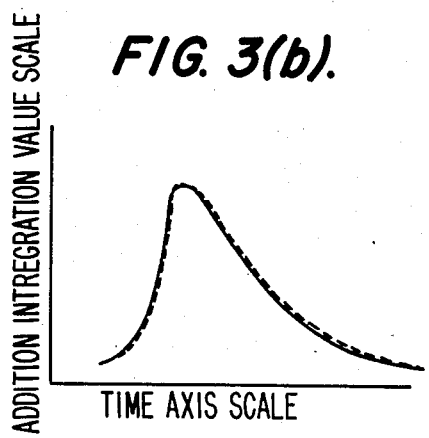
Figure 3C:
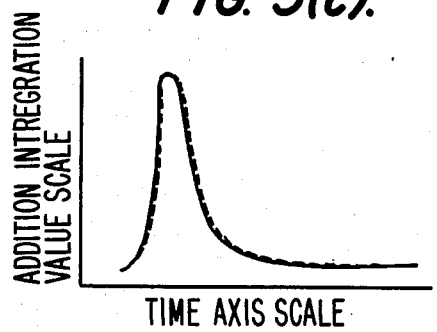

Next, the procedure for eliminating the shift between two shapes on the time-axis will be described. At first, the measurement is carried on an optical scatterer in place of the sample (6). At this juncture, since the shapes obtained by the multichannel pulse height analyzers (14) and (15) are similarly excited light shapes, they appear as the same shape shifted on the time-axis on the two-picture synthetic display (16), as shown by a full line and a broken line in FIG. 3(a). If the correcting potentiometer (13) is operated, the offset voltage $V_{off}$ is changed, so that one of the shapes on said display (16) is shifted to the right or left along the time-axis. The correcting potentioneter (13) is operated while watching the display (16) so as to make two shapes coincide with each other, as shown in FIG. 3(b). Thus, the correction of the shift on the time-axis is finished. Subsequently, the measurement is carried out on the sample (6) in place of the optical scatterer to obtain the excitation light shaped $P_{(t)}$ and the luminescence transient shape $I_{(t)}$ which are not effected by the difference between the lengths of light passages. In addition, FIG. 3(c) shows the relative positional relation of two shapes in the case where the time-range was changed-over after two shapes has been made to coincide with each other as shown in FIG. 3(b).

What is claimed is:

1. An apparatus for measuring the luminescence lifetime of a sample comprising:
   a light source for generating an excitation light pulse;
   a start pulse generator means for generating a start pulse in response to a leading edge of said excitation light pulse;
   a first stop pulse generator for generating a first stop pulse in response to a trailing edge of said excitation pulse;
   a second stop pulse generator for generating a second stop pulse in response to a fluorescence light pulse output from the sample when said excitation light pulse impinges thereon;
   first and second time to voltage converters connected to said start pulse generator means for receiving said start pulse output therefrom and respectively connected to said first and second stop pulse generators for respectively receiving said first and second stop pulses therefrom, said first and second time to voltage converters respectively outputting voltages proportional to the time between said start pulse and said first and second stop pulses;
   a variable offset voltage generator and an adder means, an output of said variable voltage generator and an output of said first time to voltage converter being added together by said adder means;
   first and second pulse height analyzers respectively connected to said adder means and said second time to voltage converter for analyzing outputs therefrom;
   a two-picture synthetic display means connected to said first and second pulse height analyzers for simultaneously displaying outputs therefrom;
   wherein said excitation light pulse waveshape and said fluorescence luminance light pulse waveshape are simultaneously measured by said first and second time to voltage converters and wherein said variable offset voltage generator output is varied in accordance with a range of said apparatus, whereby time axes of said apparatus are automatically changed with corresponding changes in the range of said apparatus.

* * * * *